United States Patent [19]

Verhoeven et al.

[11] Patent Number: 4,645,854

[45] Date of Patent: Feb. 24, 1987

[54] PROCESS FOR PREPARING HMG-COA REDUCTASE INHIBITORS WITH A 3,5-DIHYDROXYPENTANOATE SUBUNIT

[75] Inventors: Thomas R. Verhoeven, Cranford; James M. McNamara, Rahway; Meyer Sletzinger, North Plainfield, all of N.J.

[73] Assignee: Merck & Co., Inc., Rahway, N.J.

[21] Appl. No.: 725,891

[22] Filed: Apr. 25, 1985

[51] Int. Cl.[4] ............................................ C07C 69/767
[52] U.S. Cl. ..................................................... 560/60
[58] Field of Search ......................................... 560/60

[56] References Cited

U.S. PATENT DOCUMENTS 4,255,444 9/1980 Schmitt et al. ...................... 424/279
4,375,475 3/1983 Willard ............................... 424/279

OTHER PUBLICATIONS

Hsu et al, "J. Amer. Chem. Soc.", vol. 105, pp. 593–601 (1983).
Narasaka et al, "Chemistry Letters" (1980), 1415–1418.

*Primary Examiner*—Werren B. Lone
*Attorney, Agent, or Firm*—Joseph F. DiPrima; Michael C. Sudol

[57] ABSTRACT

A stereoselective process for the preparation of antihypercholesterolemic agents of the HMG-CoA reductase inhibitor type comprises treatment of an intermediate β-hydroxyketone with a trialkylborane and sodium borohydride at low temperatures.

4 Claims, No Drawings

PROCESS FOR PREPARING HMG-COA REDUCTASE INHIBITORS WITH A 3,5-DIHYDROXYPENTANOATE SUBUNIT

SUMMARY OF THE INVENTION

This invention is concerned with a novel stereoselective process for the preparation of antihypercholesterolemic agents of the HMG-CoA reductase inhibitor type by a stereoselective reduction of a β-hydroxyketone which can be depicted as:

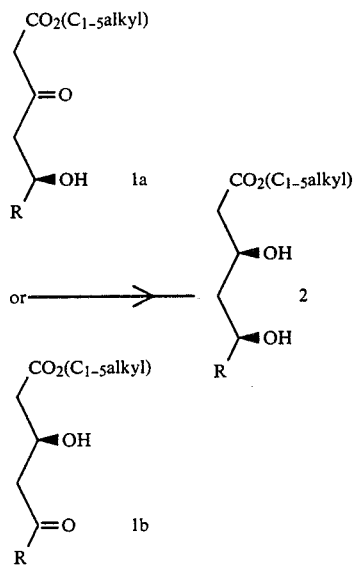

The process can be conducted in a variety of solvents, including $C_{1-4}$alkanols, at about $-100°$ C. to $-50°$ C. with a trialkyl borane and sodium borohydride.

BACKGROUND OF THE INVENTION

Hypercholesterolemia is known to be one of the prime etiological components of cardiovascular disease such as atherosclerosis, and there is still no effective antihypercholesterolemic agent available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compaction and mevinolin and a variety of semi-synthetic and totally synthetic analogs thereof. One group of totally synthetic analogs are disclosed in U.S. Pat. No. 4,375,475 and have the general structural formula:

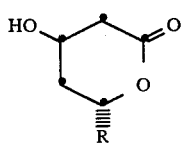

wherein R is

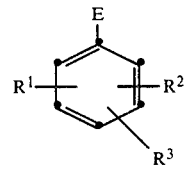

In the usual course of synthesis of these lactones an intermediate ester and dihydroxy acid are encountered:

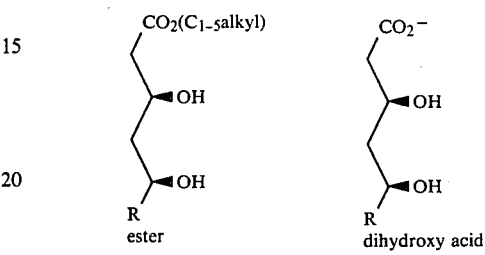

Each of these entities, as well as the lactone, demonstrate antihypercholesterolemic activity in vivo, of comparable magnitude. However, for these compounds to manifest a useful degree of activity, it is essential that the compounds have the particular 3R:5S/3S:5R steric relationship shown in the structures.

The synthesis of these compounds comprises reduction of substrates 1a or 1b

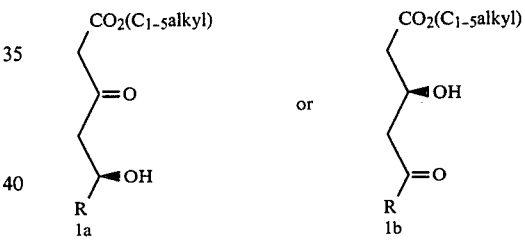

but the prior art methodology exhibited no stereoselectivity producing mixtures of the 3R,5R/3S,5S; and 3S,5R/3R,5S racemates in approximately 1:1 ratios. The enormously expensive procedures required to separate these diastereomers and the need to discard the unwanted half of the product made these products commercially unattractive.

Reduction of substrates of this type have been reported with sodium borohydride in U.S. Pat. No. 4,255,444; and with zinc borohydride by Hsu et al in *J. Amer. Chem. Sec.*, 105, 593–601 (1983); and by Narasaka et al in *Chemistry Letters*, 1415–1418 (1980) who disclosed the use of tri-n-butylborane and sodium borohydride at low temperature. The latter system provided considerable stereoselectivity, but in the examples given none of the substrates included other functional groups which could conceivably participate in the reductive process.

Now, with the present invention it is shown that the process unexpectedly is indeed applicable to compounds with a third functional group and that it is highly efficient with yields of 90% or greater and highly stereoselective, the product being better than 90% the desired diastereomer, (whereas the prior art procedures gave no better than about 60% stereoselectivity) thereby eliminating the necessity for industrially very unattractive chromatographic or other procedures for separation of isomers and making the antihypercholesterolemic agents discussed above readily available on a commercial scale.

DETAILED DESCRIPTION OF THE INVENTION

The novel process of this invention may be depicted as:

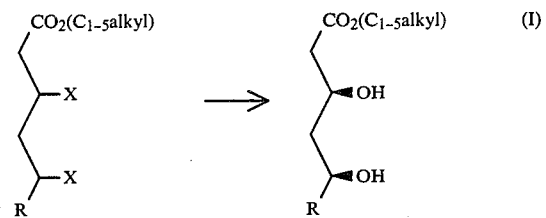

wherein one and only one X is =O and the other is OH; and R is:

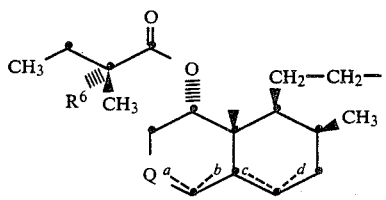

wherein Q is

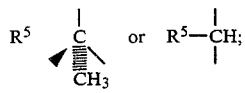

$R^5$ is H or OH; $R^6$ is hydrogen or methyl; and a, b, c, and d represent optional double bonds, especially where b and d represent double bonds or a, b, c and d are all single bonds provided that when a is a double bond, Q is

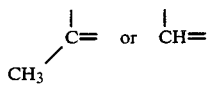

;or

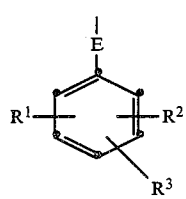

wherein E is —CH=CH— or —CH$_2$CH$_2$—; and $R^1$, $R_2$ and $R^3$ are each selected from halo such as chloro, bromo or fluoro, $C_{1-4}$alkyl, $C_{1-4}$haloalkyl, phenyl phenyl with one or more substituents independently selected from halo, $C_{1-4}$alkyl, and $C_{1-4}$alkoxy, or $R^4O$ in which $R^4$ is phenyl, halophenyl, or substituted phenyl- $C_{1-3}$alkyl wherein the substituents are selected from halo and $C_{1-4}$haloalkyl.

In a first preferred embodiment R is the radical (A). Illustrative of this embodiment are the compounds of the formula 2 wherein $R^5$ is H, $R^6$ is H or CH$_3$ and b and d represent double bonds or a, b, c and d are all single bonds.

In a second preferred embodiment, R is the radical (B). Illustrative of this embodiment are the compounds of the formula 2 wherein E is —CH=CH—, $R^1$ is in the 6-position and represents phenyl with 1 or 2 substituents independently selected from chloro, fluoro, methyl and methoxy; and $R^2$ and $R^3$ are independently selected form halo and $C_{1-3}$alkyl in the 2- and 4-positions.

In the most preferred embodiment, R is:

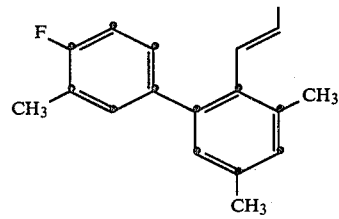

The novel process comprises the treatment of compound 1 with between 0.1 and 2.0 molecular equivalents of a tri($C_{1-4}$alkyl)borane, such as tri-ethyl-, tri-isopropyl-, tri-n-butyl-, tri-isobutyl- or tri-sec-butylborane and an activating agent such as air or pivalic acid followed by the stereospecific reduction of the dialkyl borinic acid ester with 1-2 molecular equivalents of an alkali metal borohydride, such as sodium borohydride. The process is conducted in an inert solvent such as: a hydrocarbon, e.g. hexane, toluene, cyclohexane or the like; a halocarbon, e.g. methylene chloride, chloroform, ethylene dichloride or the like; a $C_{1-4}$alkanol, e.g. methanol, ethanol, isopropanol or the like; or an ether, e.g. diethyl ether, tetrahydrofuran, 1,2-dimethoxyethane or the like; or mixtures thereof. The preferred solvent is a mixture of tetrahydrofuran and methanol in a ratio of about 1-6 volumes of tetrahydrofuran to 1 volume of methanol. When a catalytic amount of a tri($C_{1-4}$alkyl)-borane, i.e. less than 1.0 molecular equivalent, is utilized in the reduction, an $C_{1-4}$alkanol must be employed in the solvent to regenerate the tri($C_{1-4}$alkyl) borane and increase the stereoselectivity of the reaction. The reaction is conducted at temperatures between about $-100°$ C. and $-50°$ C., preferably at about $-70°$ C. for about 30 minutes to 3 hours.

A preferred process comprises the treatment of Compound 1 with between 0.10 and 0.80 molecular equivalents of a tri($C_{1-4}$alkyl)borane and between 0.01 to 0.05 molecular equivalents of pivalic acid in an inert solvent and then after cooling to between $-70°$ and $-100°$ C. adding a $C_{1-4}$alkanol followed by the addition of 1-2 molecular equivalents of an alkali metal borohydride. Under these preferred conditions greater than 90 percent of the product is in the desired stereochemical conformation.

The reaction mixture is conveniently worked up by quenching into hydrogen peroxide/water, and extracting the product into an organic solvent.

EXAMPLE 1

Preparation of Methyl
(E)-7-(4'-Fluoro-3,3',5-trimethyl[1,1'-biphenyl]-2-yl)-3,5-dihydroxy-6-heptenoate [Air Activation]

Into a glass vessel under nitrogen was charged tetrahydrofuran (22 ml), methyl E-7-(4'-fluoro-3,3',5-trimethyl[1,1'-biphenyl]-2-yl)-5-hydroxy-3-oxo-6-heptenoate (3.0 g, 7.8 mmole) and triethylborane (0.92 g, 9.4 mmole) at ambient temperature and air was bubbled through the solution. After a 5 minute age, the solution was cooled to −78° C. Sodium borohydride (350 mg, 9.25 mmole) was added followed by the addition over 15 minutes of methanol (5 ml) maintaining a temperature below −65° C. After a 30 minute age at −78° C. the mixture is carefully quenched into a rapidly stirred solution of 30% hydrogen peroxide (15 ml) and water (30 ml) at 20° C., aged 30 min then extracted with 50 ml of ethyl acetate. The organic extract was washed successively with 1N aqueous hydrochloric acid (25 ml), water (25 ml) and pH 7 buffer (25 ml), then dried over sodium sulfate (25 g). After filtration, the solution was concentrated to an oil in vacuo. Crystallization was induced by flushing with hexane, and reconcentrating in vacuo to yield the title compound in 90% assay yield (2.71 g). The product was triturated with hexanes to yield a white solid, mp. 78°–80° C. (dec). HPLC assay indicated a purity of 99%.

EXAMPLE 2

Preparation of Methyl
(E)-7-(4'-Fluoro-3,3',5-trimethyl[1,1'-biphenyl]-2-yl)-3,5-dihydroxy-6-heptenoate [Pivalic Acid Activation]

Into a glass vessel under nitrogen at ambient temperature with stirring was charged a solution of triethylborane in heptane (49.4 ml, 52.5 mmole; 15 percent w/w) and pivalic acid (255 mg, 2.5 mmole). After 90 minutes, methyl (E)-7-(4'-fluoro-3,3',5-trimethyl[1,1'-biphenyl]-2-yl)-5-hydroxy-3-oxo-6-heptenoate (19.2 g, 50.0 mmole) was charged and then dry tetrahydrofuran (170 ml) was added. After 60 minutes, the solution was cooled to −78° C. and methanol (45 ml) was added dropwise. Sodium borohydride (1.42 g, 37.5 mmole) was carefully added in three equal portions at less than −70° C. The reaction mixture was stirred at −78° C. for 2 hours and additional sodium borohydride (472 mg, 12.5 mmole) was added. After 1 hour, the cold reaction mixture was quenched by addition to 30 percent aqueous hydrogen peroxide (200 ml) while maintaining the temperature below 25° C. After 1 hour, ethyl acetate (300 ml) and water (100 ml) were added. The phases were separated and the aqueous phase was washed with ethyl acetate (50 ml). The combined organic phases were washed with 0.5M aqueous hydrochloric acid (300 ml) and then water (3×300 ml). The organic phase was dried over anhydrous sodium sulfate, filtered and concentrated in vacuo to afford the product with 98.2 percent of the desired stereochemical conformation.

EXAMPLE 3

Preparation of Methyl
(E)-7-(4'-Fluoro-3,3',5-trimethyl[1,1'-biphenyl]-3,5-dihydroxy-6-heptenoate [Catalytic Triethylborane]

In a glass vessel under nitrogen at ambient temperature with stirring was charged a solution of triethylborane in heptane (1.0 ml, 1.06 mmole; 15 percent w/w) and pivalic acid (0.10 mmole). After 60 minutes, methyl (E)-7-(4'-fluoro-3,3'-5-trimethyl[1,1'-biphenyl]-2-yl)-5-hydroxy-3-oxo-6-heptenoate (2.0 g, 5.21 mmole) and dry tetrahydrofuran (7 ml) was added. After 60 minutes the solution was cooled to −78° C. and methanol (2 ml) was added. Sodium borohydride (147 mg, 3.88 mmole) was then added and the reaction mixture stirred for 3 hours. The reaction mixture was poured into 30 percent hydrogen peroxide (15 ml) and extracted with ethyl acetate. The organic phase was dried over anhydrous sodium sulfate, filtered and concentrated in vacuo to afford the product with 90 percent of the desired stereochemical conformation.

Similarly, when 0.80 molecular equivalents of triethylborane was used in the above procedure, the product obtained was 97 percent of the desired stereochemical conformation. At 0.50 molecular equivalents of triethylborane 93 percent of the product was the desired stereochemical conformation.

EXAMPLES 4 to 13

Utilizing the general procedures of Examples 1, 2, or 3, the following compounds of the formula 2 are prepared from the appropriate starting materials.

| Compound Number | $R^1$ |
| --- | --- |
| 4 | [structure] |
| 5 | [structure] |
| 6 | [structure] |
| 7 | [structure] |
| 8 | [structure] |

-continued

| Compound Number | $R^1$ |
|---|---|
| 9 | [structure: decalin with CH3 substituents, C(=O)C(CH3)3 group, CH2CH2- linker] |
| 10 | [structure: decalin with CH3 substituents, C(=O)CH(CH3)2 group, CH2CH2- linker] |
| 11 | [structure: decalin with CH3 substituents, C(=O)C(CH3)3 group, CH2CH2- linker] |
| 12 | [structure: 4'-fluoro-3,3',5-trimethylbiphenyl with CH2CH2- linker] |
| 13 | [structure: 4-fluorobenzyloxy-dimethylphenyl with CH2CH2- linker] |

What is claimed is:

1. A process for the preparation of a compound of structural formula:

[structure 2: $CO_2(C_{1-5}alkyl)$ chain with two OH groups and R substituent]

which comprises the stereoselective reduction of a β-hydroxyketone of structural formula:

[structure 1: $CO_2(C_{1-5}alkyl)$ chain with two X groups and R substituent]

wherein one and only one X is =O and the other is OH; and R is:

[structure: phenyl ring with E, $R^1$, $R^2$, $R^3$ substituents]

wherein E is —CH=CH— or —CH$_2$—CH$_2$—; and $R^1$, $R^2$ and $R^3$ are each selected from halo, $C_{1-4}$alkyl, $C_{1-4}$haloalkyl, phenyl with one or more substituents independently selected from halo, $C_{1-4}$alkyl, and $C_{1-4}$alkoxy, or $R^4O$ in which $R^4$ is phenyl, halophenyl, or substituted phenyl-$C_{1-3}$alkyl wherein the substitutents are selected from halo and $C_{1-4}$haloalkyl; by treating compound 1 with between 0.1 and 0.8 molecular equivalents of a tri($C_{1-4}$alkyl)borane, between 0.01 and 0.05 molecular equivalents of pivalic acid, and an alkali metal borohydride in a $C_{1-4}$alkanol solvent alone in or in combination with a solvent selected from a hydrocarbon, a halocarbon, and an ether at −100° C. to −50° C. for 30 minutes to 3 hours, followed by isolation of the product 2.

2. The process of claim 1 wherein between 1.0 and 2.0 molecular equivalents of the alkali metal borohydride is utilized and the solvent is a mixture of a $C_{1-4}$alkanol and an ether.

3. The process of claim 2 wherein, E is —CH=CH—, $R^1$ is in the 6-position and represents phenyl with 1 or 2 substituents independently selected from chloro, fluoro, methyl and methoxy; and $R^2$ and $R^3$ are independently selected from halo and $C_{1-3}$alkyl in the 2- and 4-position.

4. The process of claim 3 for the preparation of (E)-7-(4'-fluoro-3,3',5-trimethyl[1,1'-biphenyl]-2-yl)-dihydroxy-6-heptenoate as a racemic mixture of the 3S,5R and 3R,5S isomers.

* * * * *